US012478752B2

(12) United States Patent
Mohamed

(10) Patent No.: US 12,478,752 B2
(45) Date of Patent: Nov. 25, 2025

(54) CPAP CANNULA DEVICE

(71) Applicant: Mohamed Aly-Helmy Mohamed, Fairfax, VA (US)

(72) Inventor: Mohamed Aly-Helmy Mohamed, Fairfax, VA (US)

( * ) Notice: Subject to any disclaimer, the term of this patent is extended or adjusted under 35 U.S.C. 154(b) by 1045 days.

(21) Appl. No.: 15/671,425

(22) Filed: Aug. 8, 2017

(65) Prior Publication Data

US 2018/0036503 A1 Feb. 8, 2018

Related U.S. Application Data

(60) Provisional application No. 62/371,978, filed on Aug. 8, 2016.

(51) Int. Cl.
*A61M 16/06* (2006.01)
*A61M 16/08* (2006.01)

(52) U.S. Cl.
CPC .... *A61M 16/0666* (2013.01); *A61M 16/0605* (2014.02); *A61M 16/0683* (2013.01); *A61M 16/0858* (2014.02); *A61M 2210/0618* (2013.01)

(58) Field of Classification Search
CPC .......... A61M 16/0666; A61M 16/0605; A61M 16/0683; A61M 16/0858; A61M 2210/0618
See application file for complete search history.

(56) References Cited

U.S. PATENT DOCUMENTS

| | | | | |
|---|---|---|---|---|
| 5,682,881 A * | 11/1997 | Winthrop | A61M 16/0666 | 128/200.26 |
| 6,776,162 B2 * | 8/2004 | Wood | A61M 16/0666 | 128/207.13 |
| 8,833,372 B2 | 9/2014 | Han et al. | | |
| 2002/0059935 A1 * | 5/2002 | Wood | A61M 16/0666 | 128/207.18 |
| 2003/0047185 A1 * | 3/2003 | Olsen | A61M 16/06 | 128/203.22 |
| 2004/0025885 A1 * | 2/2004 | Payne, Jr. | A61F 5/56 | 128/848 |
| 2004/0226566 A1 * | 11/2004 | Gunaratnam | A61M 16/0666 | 128/207.18 |
| 2005/0066976 A1 | 3/2005 | Wondka | | |
| 2005/0092329 A1 | 5/2005 | Sta-Maria | | |
| 2006/0137013 A1 | 6/2006 | Lok | | |

(Continued)

FOREIGN PATENT DOCUMENTS

WO WO-2016108116 A1 * 7/2016 ............ A61M 16/06

*Primary Examiner* — Victoria Murphy
(74) *Attorney, Agent, or Firm* — Sughrue Mion, PLLC

(57) ABSTRACT

A continuous positive airway pressure (CPAP) cannula device that comprises two respiratory tubes and a nasal interface comprising two nasal prongs. The two respiratory tubes and the nasal interface may have a D-shaped cross-sectional design in which a flat part thereof rests against a patient's face. The continuous positive airway pressure (CPAP) cannula device may further comprise a one-piece design. The continuous positive airway pressure (CPAP) cannula device may be formed so as to not require complex securing means to secure the device to a patient. The continuous positive airway pressure (CPAP) cannula device may further comprise a clip to secure the respiratory tubes together at a position at the back of a patient's head.

21 Claims, 18 Drawing Sheets

(56) References Cited

U.S. PATENT DOCUMENTS

| | | | | |
|---|---|---|---|---|
| 2008/0011305 | A1* | 1/2008 | Chandran | A61M 16/0666 128/207.18 |
| 2009/0032018 | A1* | 2/2009 | Eaton | A61M 16/0683 128/201.22 |
| 2010/0018534 | A1* | 1/2010 | Veliss | A61M 16/06 128/206.24 |
| 2010/0132716 | A1* | 6/2010 | Selvarajan | A61M 16/0683 128/207.18 |
| 2011/0067704 | A1* | 3/2011 | Kooij | A61M 16/0666 128/207.18 |
| 2015/0083123 | A1* | 3/2015 | Tero | A61M 16/0875 128/202.27 |

* cited by examiner

CPAP CANNULA DEVICE

The present Application claims priority to U.S. provisional Application No. 62/371,978, filed Aug. 8, 2016, which is incorporated in its entirety herein by reference.

BACKGROUND OF THE INVENTION

The present Application relates to a nasal interface device configured for use with a Continuous Flow Positive Airway Pressure (CPAP) device, a Variable Flow Positive Airway Pressure device, or mechanical ventilators to provide non-invasive ventilation. More specifically, the present Application relates to a non-invasive ventilation device with a nasal interface or nasal prongs or cannula. That is, the present Application relates to a CPAP cannula device. The CPAP cannula device is primarily designed to treat individuals, especially neonates (young infants) who have compromised respiratory systems and who require respiratory intervention either with non-invasive CPAP or non-invasive positive pressure ventilation to assist their breathing.

Currently, Continuous Flow Positive Airway Pressure (CPAP) is used to provide non-invasive respiratory support (non-invasive ventilation) to adult and pediatric patients with mild to moderately compromised respiratory systems.

For example, CPAP is often necessary to treat adult patients having obstructive sleep apnea and/or chronic emphysema. With regards to neonates, that is, young infants, disorders necessitating CPAP application include, for example, respiratory distress syndrome (RDS), transient tachypnea of the newborn (TTN), pneumonia, and chronic pulmonary insufficiency. These disorders are noted only as examples; CPAP is used to treat a variety of other causes resulting in compromised patient respiratory systems.

CPAP application provides respiratory support (non-invasive ventilation) in both adult and pediatric populations by delivering sustained distending low pressure to collapsed alveoli using an air-oxygen mixture. Such intervention eventually improves functional residual alveolar capacity and therefore decreases the amount of human work needed to inflate the lungs, thereby reducing the amount of human breathing work needed to deliver oxygen to the body, and wash carbon dioxide from the body and therefore alleviate the need for more invasive ventilatory support using mechanical ventilation.

Traditionally, CPAP has been provided to patients using several methods including endotracheal intubation, long nasopharyngeal tube intubation, face and nasal masks, nasal prongs, high flow nasal cannula, as well as combinations thereof; such as a combined nasal mask with nasal prongs incorporated therein. Each of the above-described methods currently in use however contains several drawbacks.

For example, endotracheal intubation, which is an invasive procedure that sometimes requires putting patients to sleep under heavy sedation, is associated with several complications including air leaks, infections, increased hospital stays, and most dangerously chronic lung disease.

Nasopharyngeal tube intubation, which is less invasive than endotracheal intubation, involves the use of a single tube passed through an individual's nares until the tip of the intubation tube reaches the posterior pharynx. Although, this method is less invasive than endotracheal intubation, nasopharyngeal tube intubation is associated with increased resistance during expiration and results in an increased amount of work during breathing and is also associated with an increased rate of infection and ulcerations.

CPAP delivered via nasal or face masks, or via nasal interfaces with nasal prongs is traditionally less invasive than both endotracheal intubation and nasopharyngeal tube intubation but is cumbersome and unwieldy. That is, is it difficult to keep the nasal or face masks, or the nasal prongs in a position on a patient that secures delivering the right amount of pressure at all times. Currently, available CPAP systems are made of several pieces that have to be put together, taped, or pinned to a hat or stabilizing cover and require frequent checking and careful attention to its assembly. Further such systems have components that frequently disconnect.

High flow nasal cannula is a nasal cannula interface comprising long thin nasal prongs that go into both nares to provide a high flow air-oxygen mixture. It is intended to provide flow-dependent CPAP. These types of devices do not completely seal the patient's nose and therefore the pressure generated is unpredictable. That is, it is difficult to maintain a non-fluctuating air pressure in this system. The nasal prongs on these types of devices are of a relatively narrow diameter (occluding only 60-80% of the nares), as compared to standard CPAP nasal prongs (occluding approximately 100% of the nares), thus the airflow for the nasal cannula will need to be higher to deliver the same pressure compared to the standard CPAP prongs. However, it still remains difficult to maintain a non-fluctuating air pressure in this system, even with higher delivered flow. Therefore the outcomes obtained from high flow nasal cannula are suboptimal to those obtained from CPAP systems in regards, for example, to preventing chronic lung disease.

Of the systems/methods used to deliver CPAP discussed above, systems/devices comprising nasal prongs, have been the ones commonly used and have provided the most effective methods to deliver CPAP to pediatric and adult patient populations. There have been many developments and different versions of these types of systems developed in recent years. A typical example of a modern CPAP system/device comprising a nasal interface with nasal prongs used to deliver CPAP to a neonate will now be described.

Patent literature 1 describes a conventional nasal interface with nasal prongs 100 used to deliver CPAP to a neonate patient. FIGS. 1 and 2 depict this conventional nasal interface 100. This conventional system comprises nasal prongs 94a and 94b, which are inserted into the neonate's nares, a connecting nasal interface 93, connecting elbows 112a and 114a, which connect the nasal interface 93 to the corrugated respiratory tubes 112 and 114. The corrugated respiratory tubes 112 and 114 are connected to a gas source (not shown) and are respectively for inspiratory and expiratory functions. In order to secure the system/device to a neonate in a stable position, the system/device must be secured by a securing means 144 , which secures the respiratory tubes 112 and 114 to a second securing means 124 (e.g. a hat in the shown conventional system/device). The hat 124 is further secured around the neonate patient by a chin securing strap 146. In this conventional example, the securing means 144, and 146 are secured via Velcro® brand hook and loop type fasteners. As is shown in FIG. 1, since the nasal prongs 94a and 94b extend perpendicularly from the nasal interface 93 and are essentially parallel to the respiratory tubes 112, and 114, the conventional nasal interface with nasal prongs 100 must be positioned on the neonates head in a substantially forward manner.

In addition to the securing means depicted in FIGS. 1 and 2 for use in the conventional face mask with nasal prongs 100, pins, tapes, or other special connectors to fix the system in a stable position are also conventionally used. That is, practitioners typically use whatever securing means are available to secure the conventional face mask with nasal prongs to a neonate. Further, a protectant (such as Cannulaide® or Duaderm®) to be applied to the patient's skin for protection (not shown) is also typically used.

As discussed above, conventional nasal interface devices with nasal prongs (and nasal or face mask alike) typically used to deliver CPAP have the problem of being difficult to maintain a position on a patient's face/head. This is particularly a problem for neonate patients, who have smaller heads and smaller nares than adult patients, and always move around or try to take the prongs off. In addition to being difficult to maintain in a stable position on the patient, the components of a conventional system with nasal prongs used to deliver CPAP may also inadvertently injure the patient by causing nasal septum erosions.

For example, as is shown in FIGS. 1 and 2, since the respiratory tubes 112 and 114 comprise corrugated tubes, there is the problem that the tube will rub against the patient's face, irritating the skin. Further, since the nasal prongs 94a and 94b are formed in a cylindrical shape and are connected to the connecting nasal interface 93, which also comprises a cylindrical tube, the nasal prongs 94a and 94b and connecting nasal interface 93 may rub against the patient's upper lip and nasal septum causing irritation to the patient's skin or more seriously exert pressure on the nasal septum from outside causing nasal septum erosions or damage.

Nasal interfaces with nasal prongs suffer the same drawbacks as described above with respect to face masks used to deliver CPAP. Thus although, nasal or face masks and nasal interfaces with nasal prongs are more advantageous to deliver CPAP over intubation and mechanical ventilation, and nasal cannula in neonates and infants with mild to moderate compromised respiratory systems or respiratory distress, wide-spread use of nasal and/or face masks and nasal prongs CPAP has been impeded by the complexity of application and the drawbacks discussed above. That is, the extensive labor and effort required to put the aforementioned conventional nasal and/or face masks and nasal interfaces with nasal prongs to use, apply and fix it to the patient's (particularly a neonate) nose/face has traditionally prevented a more widespread application thereof.

In addition, it is difficult and labor intensive to maintain all these pieces fixed in place and connected together to efficiently deliver uninterrupted flow of gas under pressure to the neonate's respiratory system.

Further still, even those patients who are managed with intubation and mechanical ventilation for an initial period but thereafter managed with nasal cannula often suffer from increased incidence of chronic lung disease.

The instant disclosure has been developed in light of the above problems, and is directed to a Continuous Positive Airway Pressure (CPAP) cannula device.

CITATION LIST

Patent literature

Patent literature 1: U.S. Pat. No. 1,0752,069

SUMMARY OF THE INVENTION

One aspect of the disclosure is a continuous positive airway pressure (CPAP) cannula device comprising a first respiratory tube and a second respiratory tube; a nasal interface tube provided between the first and second respiratory tubes; and two nasal prongs extending radially from the nasal interface tube; wherein the respiratory tubes, the nasal interface, and the nasal prongs are integrated with each other so as to comprise a one-piece design.

The continuous positive airway pressure (CPAP) cannula device may further be configured such that each of the two respiratory tubes has a D-shaped cross section, such that a flat part of the D-shaped cross section is configured to rest against a patient's face and head; and the nasal interface tube may also have a D-shaped cross section comprising a nasal segment flat base portion and a nasal segment curved portion, wherein the nasal segment flat base portion is configured to rest against the patient's face and upper lip.

The continuous positive airway pressure (CPAP) cannula device may also be configured such that each of the two nasal prongs comprises a nasal upperside length and a nasal underside length. In one embodiment, the nasal upperside length may be longer than the nasal underside length.

The continuous positive airway pressure (CPAP) cannula device may also further comprise a first transitioning segment and a second transitioning segment, wherein the first transitioning segment connects the nasal interface tube on one end to the first respiratory tube, and the second transitioning segment connects the nasal interface tube on the other end to the second respiratory tube.

Further, each of the respiratory tubes may have a similar or larger diameter than the nasal interface tube.

In addition, the nasal interface tube may have a similar or different cross-sectional shape than each of the respiratory tubes.

A second aspect of the disclosure is a continuous positive airway pressure (CPAP) cannula device comprising: a first respiratory tube and a second respiratory tube; a nasal interface tube provided between the first and second respiratory tubes; and two nasal prongs extending radially from the nasal interface tube; wherein each of the two nasal prongs comprise a nasal upperside length and a nasal underside length; wherein the nasal upperside length may be longer than the nasal underside length.

A third aspect of the disclosure is a continuous positive airway pressure (CPAP) cannula device comprising a first respiratory tube and a second respiratory tube; a nasal interface tube provided between the first and second respiratory tubes; and two nasal prongs extending radially from the nasal interface tube; wherein each of the two respiratory tubes has a D-shaped cross section, such that a flat part of the D-shaped cross section is configured to rest against a patient's face and head; wherein the nasal interface tube has a D-shaped cross section comprising a nasal segment flat base portion and a nasal segment curved portion, such that the nasal segment flat base portion is configured to rest against the patient's face and upper lip.

The continuous positive airway pressure (CPAP) cannula device may further be configured such that each of the two nasal prongs initially extend in a radial direction parallel to the nasal segment flat base portion before curving toward a direction perpendicular to the nasal segment flat base portion.

The continuous positive airway pressure (CPAP) cannula device according to the instant embodiment may also be configured such that the respiratory tubes, the nasal interface, and the nasal prongs are integrated with each other so as to comprise a one-piece design.

The continuous positive airway pressure (CPAP) cannula device according to the instant embodiment may also be configured such that each of the two respiratory tubes are configured to wrap around the patient's face from a position corresponding to the patient's cheeks to a position on the back upper part of the patient's head.

The continuous positive airway pressure (CPAP) cannula device according to the instant embodiment may also be configured to further comprise a clip; wherein each of the two respiratory tubes converge toward each other at a position on a back upper part of the patient's head and they rest against each other on their flat surfaces and are secured to each other at the position on the back upper part of the patient's head by the clip.

The continuous positive airway pressure (CPAP) cannula device according to the instant embodiment may also be configured such that the nasal interface is indented in between the nasal prongs.

DETAILED DESCRIPTION OF THE INVENTION

Hereinafter, a preferred embodiment of the CPAP cannula device will now be described with reference to the drawings.

Figure 1:
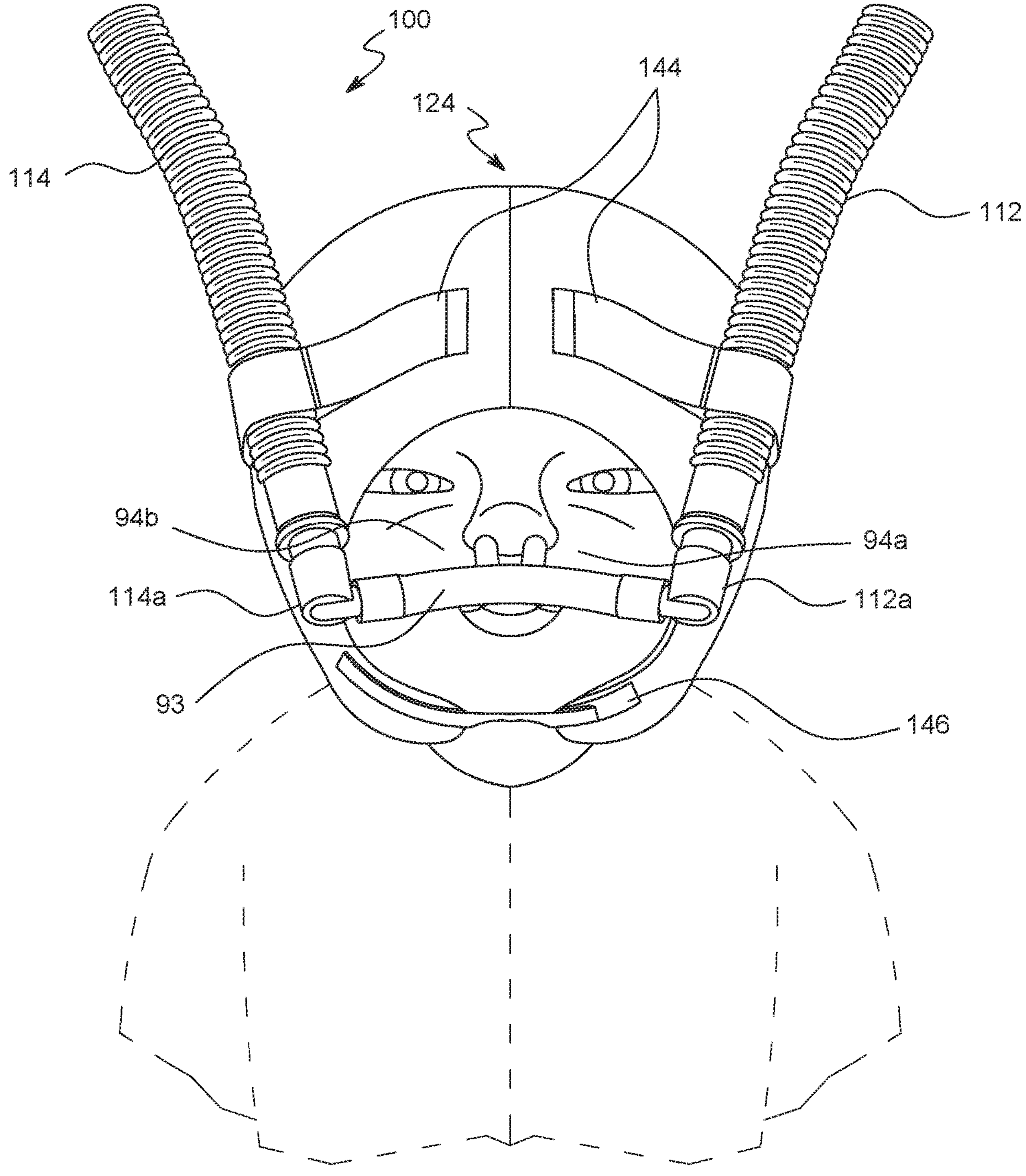
FIG. 1 is a front view of a conventional CPAP system/device comprising nasal prongs as applied to a neonate patient.
Figure 2:
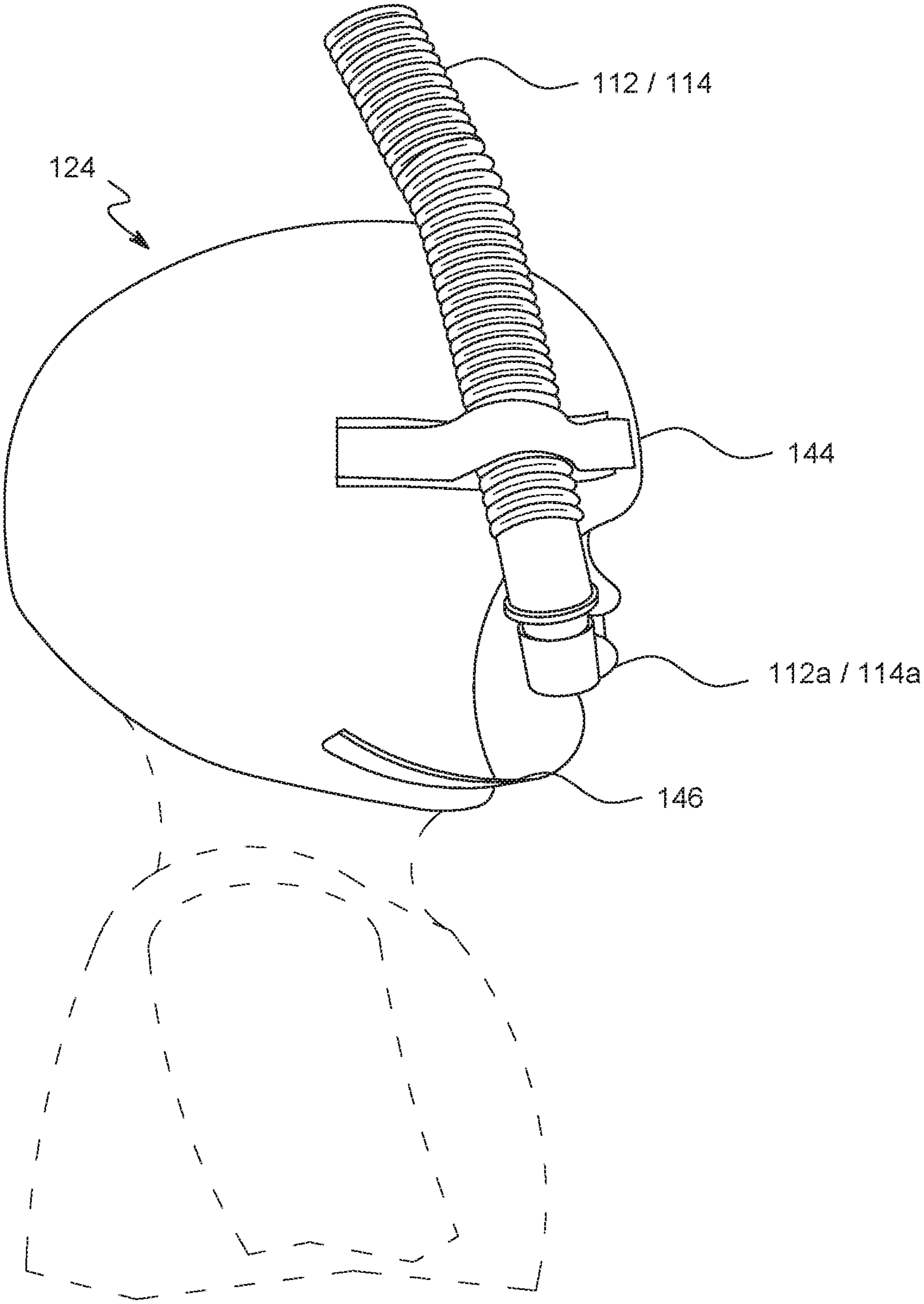
FIG. 2 is a side view of a conventional CPAP system/device comprising nasal prongs as applied to a neonate patient.
Figure 3:
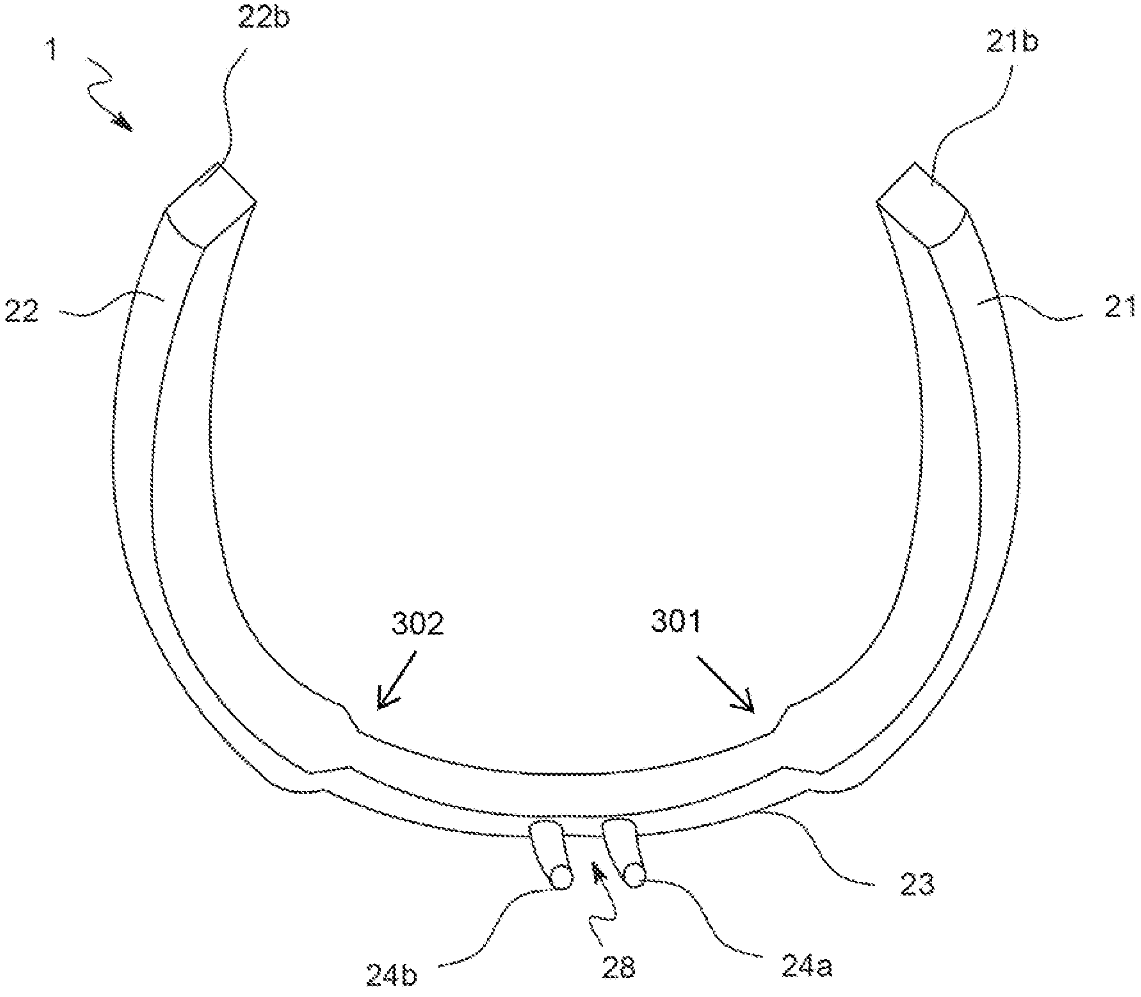
FIG. 3 is an oblique view of the continuous positive airway pressure (CPAP) cannula device according to the preferred embodiment.
Figure 4:
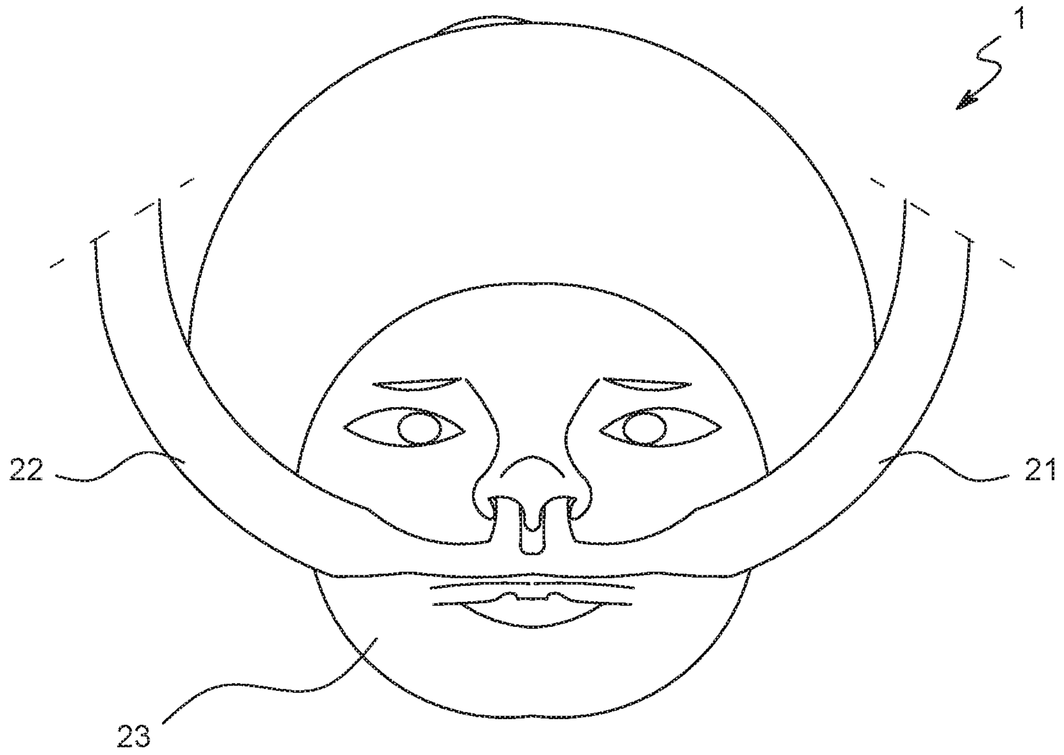
FIG. 4 is a front view of the continuous positive airway pressure (CPAP) cannula device according to the preferred embodiment as the device is applied to a neonate patient.
Figure 5:
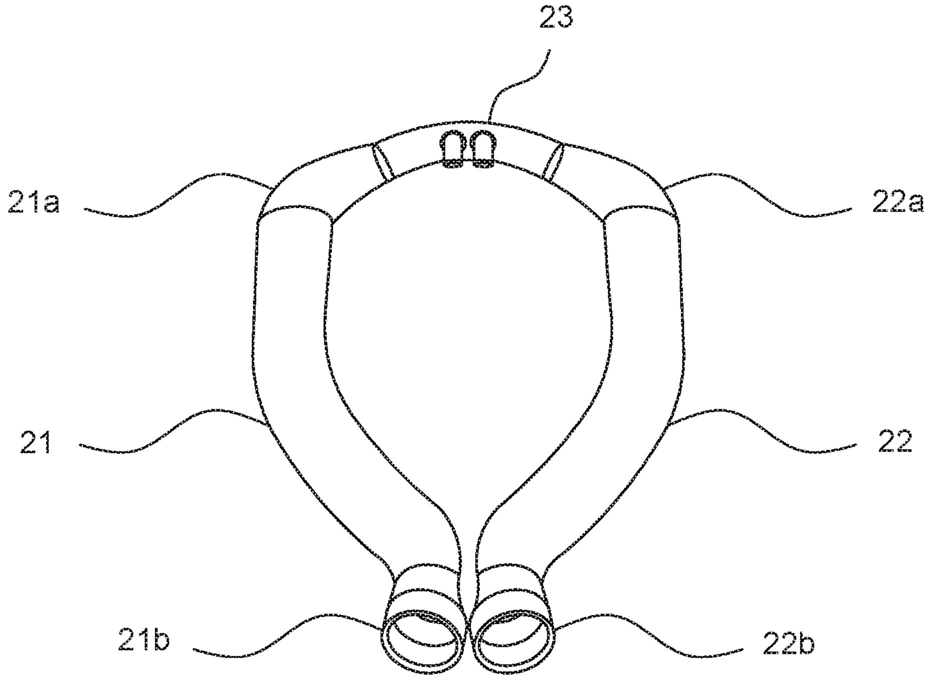
FIG. 5 is an oblique view of the continuous positive airway pressure (CPAP) cannula device according to the preferred embodiment.

As is shown in FIGS. 3-5, the CPAP cannula device 1 comprises two respiratory tubes 21 and 22. One of the two respiratory tubes 21 and 22 is for patient inspiration and the other one of the two respiratory tubes 21 and 22 is for patient expiration. Both of the respiratory tubes 21 and 22 may be connected to a ventilation device (not shown), or the inspiratory tube may be connected to a gas source (not shown) while the expiratory tube may be either connected to a valve (not shown) or immersed under water seal (not shown). The optional but preferable gas source provides a continuous positive airway pressure of an air-oxygen mixture.

As is shown in FIG. 3-5, each of the two respiratory tubes 21 and 22 are connected at one end thereof to a nasal interface 23. That is, the nasal interface 23 is connected to both respiratory tubes 21 and 22. The connection between the respiratory tubes 21 and 22 and the nasal interface 23 is a smooth connection such that no material juts out from the connected portion. This connection will be described in more detail later. Further, the connection between the respiratory tubes 21 and 22 and the nasal interface 23 is provided such that the respiratory tubes 21 and 22 and the nasal interface 23 form a one-piece design.

Specifically regarding the one-piece design, it will be noticed that, when referring to FIG. 3, the CPAP cannula device is shaped into a continuous, substantially U-shape. Further, although formed of a one-piece design, the CPAP cannula device according to the preferred embodiment is flexible such that the device can be fitted around patients with different sized heads.

This one-piece design (as opposed to conventional CPAP ventilation systems/devices which have multiple pieces connected together that need to be disassembled/reassembled before every use) avoids unnecessary sophistication and complexity in application and maintenance thereof. Thus, the one piece design provides a user-friendly device that does not require special training to be administered. Further, the one-piece design of the instant CPAP cannula device according to the instantly described embodiment facilitates the use thereof by a wide spectrum of users, from trained health care practitioners to non-such-trained individuals, and allows for use in different settings including hospital, clinics, as well the patient's homes.

Figure 6A:
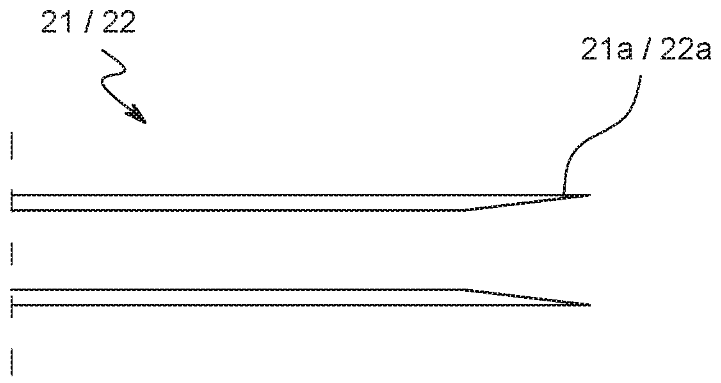
FIG. 6*a* is partial view of one of the respiratory tubes of the continuous positive airway pressure (CPAP) cannula device.
Figure 6B:
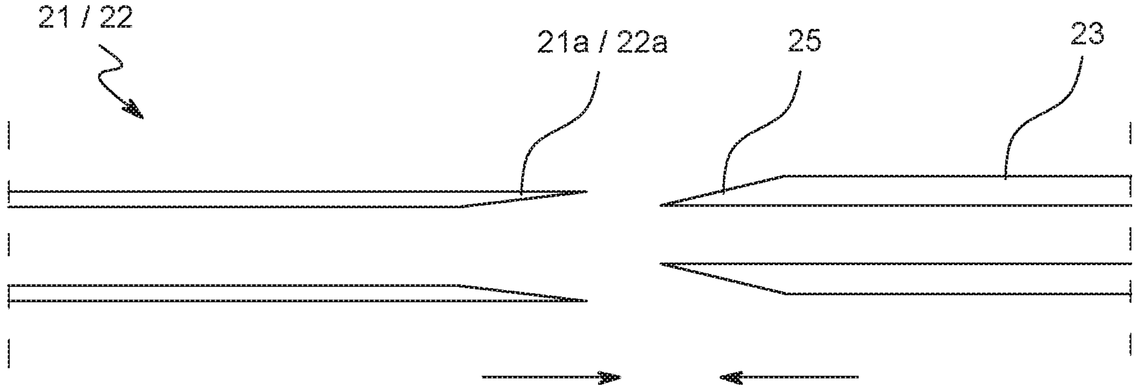
FIG. 6*b* is a partial view of one of the respiratory tubes and a distal end of the nasal interface of the continuous positive airway pressure (CPAP) cannula device.

Referring now to the connection between the respiratory tubes 21 and 22 and the nasal interface 23, it will be noticed when referring to FIG. 6*a*, that the connecting portions 21*a* and 22*a* of the respiratory tubes 21 and 22, have outer sidewalls and inner sidewalls, such that the inner sidewalls converge toward the outer sidewalls at the distal end of the respective connecting portions 21*a* and 22*a*. It will also be noticed that when referring to FIG. 6*b*, that the extension portions 25 of the nasal interface 23 have outer sidewalls and inner sidewalls, such that the outer sidewalls converge toward the inner sidewalls at the distal end of each of the extension portions 25. During manufacturing of the CPAP cannula device, the connecting portions 21*a* and 22*a* of the respiratory tubes 21 and 22, respectively, each connect to an extension portion 25 of the nasal interface 23 in the direction of the arrows shown in FIG. 6*b*. That is, when the nasal interface 23 is connected to each of the respiratory tubes 21 and 22, the outer sidewalls of the extension portions 25 of the nasal interface 23 abut against the inner side walls of the connecting portions 21*a* and 22*a* of the respiratory tubes 21 and 22, respectively. Such a connection forms a seamless connection such that no material juts outs of the connection. While in the preferred embodiment the extension portion 25 of the nasal interface 23 fits into the connecting portions 21*a* and 22*a* of the respiratory tubes 21 and 22, respectively, the connection may be reversed. That is, the connecting portions 21*a* and 22*a* of the respiratory tubes 21 and 22, respectively, may fit into the extension portions 25 of the nasal interface 23. Further, although the connection has been described with varying inner and outer sidewalls, the connection may be realized via other means, such as interlocking fingers, so long as the connection forms a seamless connection between the parts of the CPAP cannula device. Alternatively, a connection that does not form a seamless connection may be used.

In the preferred embodiment, as is shown in FIG. 3, the respiratory tubes 21 and 22 may have a different cross-sectional shape and a different cross-sectional diameter than the nasal interface 23. Accordingly, the extension interfaces 25 of the nasal interface 23 are preferably configured so as to connect the respiratory tubes 21 and 22 to the nasal interface 23, even when the respiratory tubes 21 and 22 have a different cross-sectional shape and/or diameter than the nasal interface 23. Of course, the extension interfaces 25 may also connect the respiratory tubes 21 and 22 to the nasal interface 23 when the respiratory tubes 21 and 22 have the same cross-sectional design and shape as that of the nasal interface 23. The extension interfaces 25 may also constitute the same cross-sectional shape and/or size as that of the respiratory tubes 21 and 22 and/or the nasal interface 23 in order to obtain the benefits thereof described herein.

As is shown in FIGS. 3, 4, 8*a*, and 8*b*, the nasal interface 23 comprises two nasal prongs 24*a* and 24*b* integrally formed in a center portion of the nasal interface 23. Between the nasal prongs 24*a* and 24*b* is the nasal prongs intra distance 28, which may be changed (i.e. lengthened or shortened) in order to fit the CPAP cannula device to patients of different sizes.

Figure 7:
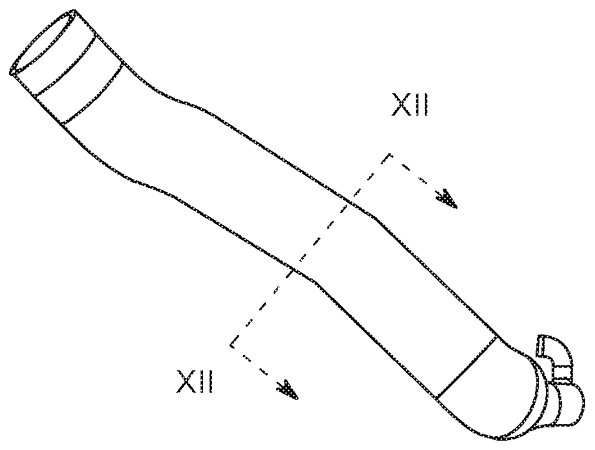
FIG. 7 is a side view of the continuous positive airway pressure (CPAP) cannula device according to the preferred embodiment.
Figure 10:
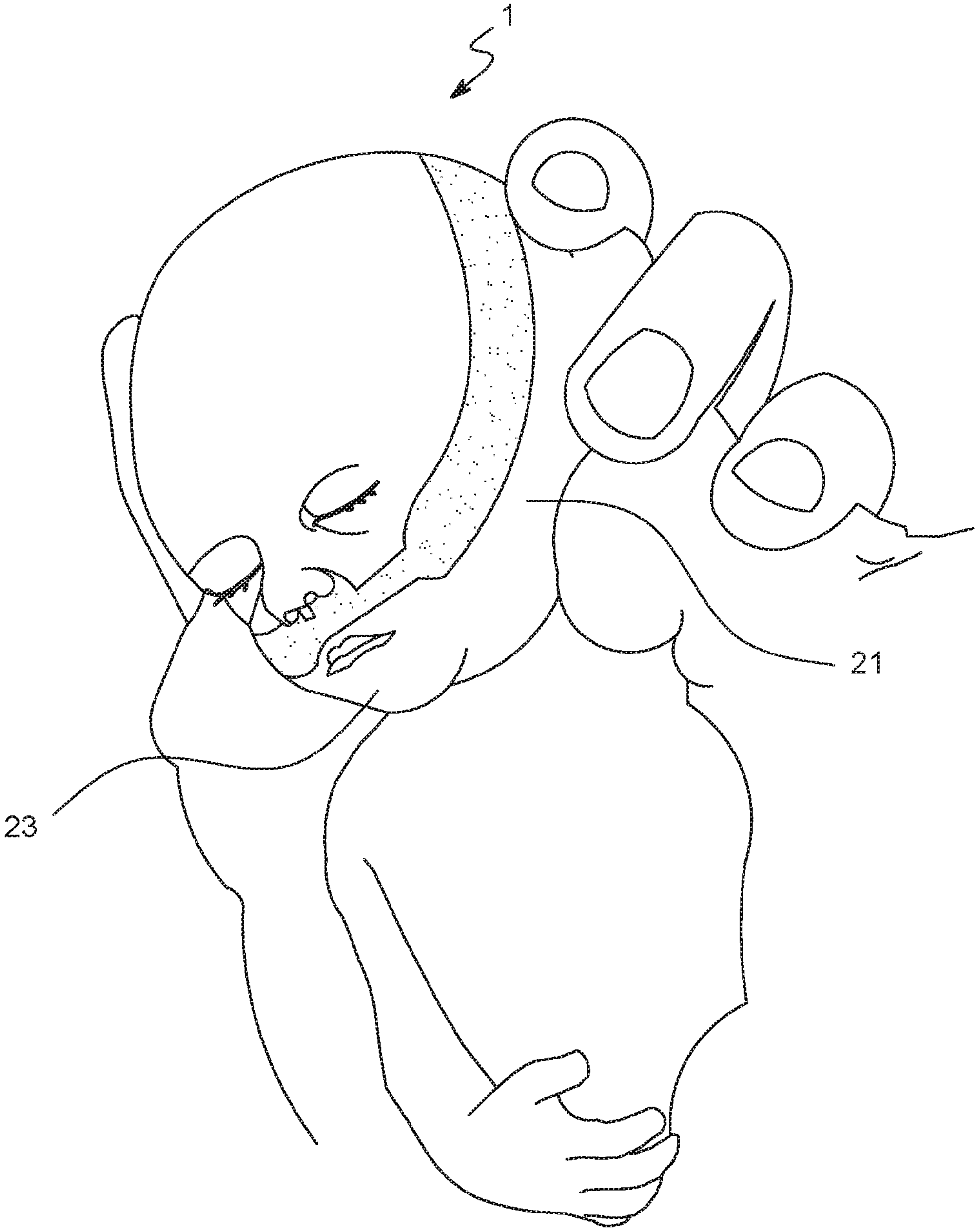
FIG. 10 is a view of a neonate, wherein the shaded portion on the neonate represents the preferred placement location of the continuous positive airway pressure (CPAP) cannula device according to the preferred embodiment.

Referring again to the respiratory tubes 21 and 22, as is shown in FIGS. 4 and 10, the respiratory tubes 21 and 22 are configured to wrap around a patient's (e.g. a neonate, as is shown FIGS. 4 and 10) head from a position on the patient's upper cheek, where the respiratory tubes 21 and 22 are configured to respectively connect to the nasal interface 23, to a position on the back upper part of the patient's head. That is, each of the respiratory tubes 21 and 22 may include a curved portion shaped and configured to follow a curve of a patient's face in a backward and upward direction, from a position corresponding to the patient's cheeks to a position on a back upper part of the patient's head; e.g., from respective portions connecting to the nasal interface 23, each of the first and second respiratory tubes 21 and 22 is shaped to extend in a direction perpendicular to a direction in which the nasal interface extends 23, and perpendicular to the direction in which the nasal prongs 24*a* and 24*b* extend from the nasal interface 23, before extending to a position corresponding to the patient's cheeks to a position corresponding to a back upper part of the patient's head. In other words, the respiratory tubes 21 and 22 may be shaped and configured to follow a contour of a patient's face along the patient's cheeks to a position on a back upper part of the patient's head. Further, as is shown in FIGS. 5 and 7, each of the two respiratory tubes 21 and 22 comprise a connecting portion 21*a* and 22*a*, respectively for connecting to the nasal interface 23. These respective connecting portions 21*a* and 22*a* are positioned at a location corresponding to the upper cheek. Referring now to FIGS. 4 and 10, each of the respiratory tubes 21 and 22 then curve from the respective connecting portions 21*a* and 22*a* in a predetermined angle corresponding to the radius of curvature of a typical (i.e. a neonate) patient's head toward the back upper part of the patient's head so as to converge toward each other. As is shown in FIGS. 3 and 5, after the two respiratory tubes 21 and 22 converge at a converging point corresponding to respective converging portions 21*b* and 22*b*, the two respiratory tubes 21 and 22 extend in a direction away from a patient's head in a direction perpendicular to the patient's head.

That is, each of the two respiratory tubes 21 and 22 converge at a converging point corresponding to respective converging portions 21*b* and 22*b* at a position that is preferably between the occiput and vertex of the rear of the patient's head. However, the converging point may be below the occiput or above the vertex. After converging, each of the two respiratory tubes 21 and 22 extend in a predetermined distance beyond the patient's head in a substantially perpendicular manner before being connected to a gas source and pressure generating tool (a valve or under water seal), or to a ventilator (not shown), as per the preferred embodiment.

Figure 11A:
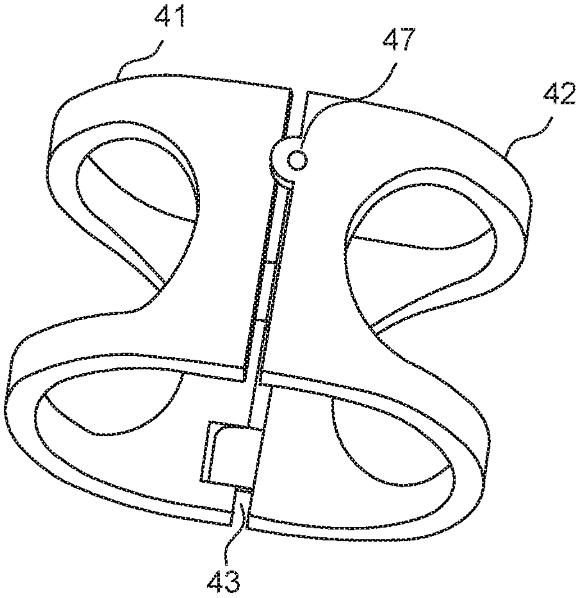
FIG. 11*a* is a view of the clamp of the continuous positive airway pressure (CPAP) cannula device according to the preferred embodiment when the clamp is in a latched state.
Figure 11B:
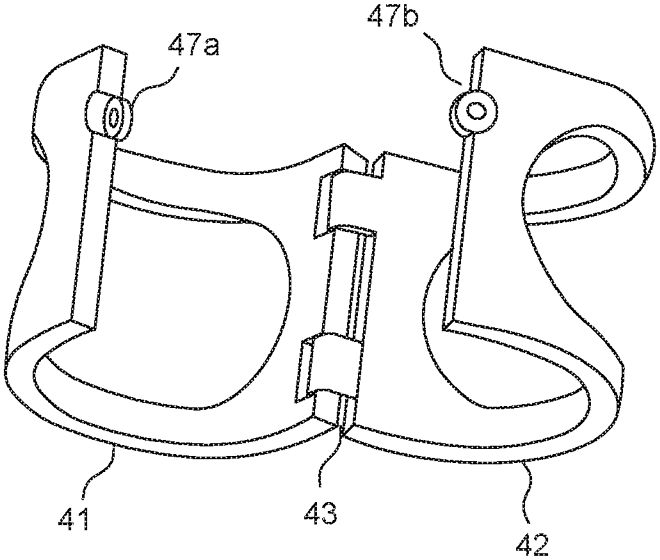
FIG. 11*b* is a view of the clamp of the continuous positive airway pressure (CPAP) cannula device according to the preferred embodiment when the clamp is in an unlatched state.

At a converging point corresponding to respective converging portions 21*b* and 22*b*, the two respiratory tubes 21 and 22 may be held together by a clamp 40. The clamp 40 will now be described with reference to FIGS. 11*a* and 11*b*. The clamp 40 comprises two swinging portions 41 and 42, each secured at one end via a hinge 43. The hinge 43 allows the two swinging portions 41 and 42 to freely rotate about a fixed axis. The swinging portions 41 and 42 wrap around the two respiratory tubes 21 and 22 where flat surface of each respiratory tube (21, 22) rests on the other respiratory tube (21, 22) when the clamp is in a latched state, as is shown in FIG. 11*a* (omitting the respiratory tubes 21 and 22 from view). That is, as is shown in FIG. 11*a*, the swinging portions 41 and 42 are configured to be latched together in a locking manner via a mating device 47. The swinging portions 41 and 42 are also configured to be in an open state when the clamp 40 is unlatched, as is shown in FIG. 11*b*. The mating device 47 comprises a pin 47*a* disposed on one of the swinging portions 41 and 42, and a corresponding pin hole 47*b* disposed on the other of the swinging portions 41 and 42. The mating device 47 is further configured to be latched when the pin 47*a* enters the pin hole 47*b*, and unlatched when the pin 47*a* is removed from the pin hole 47*b*.

Figure 11C:
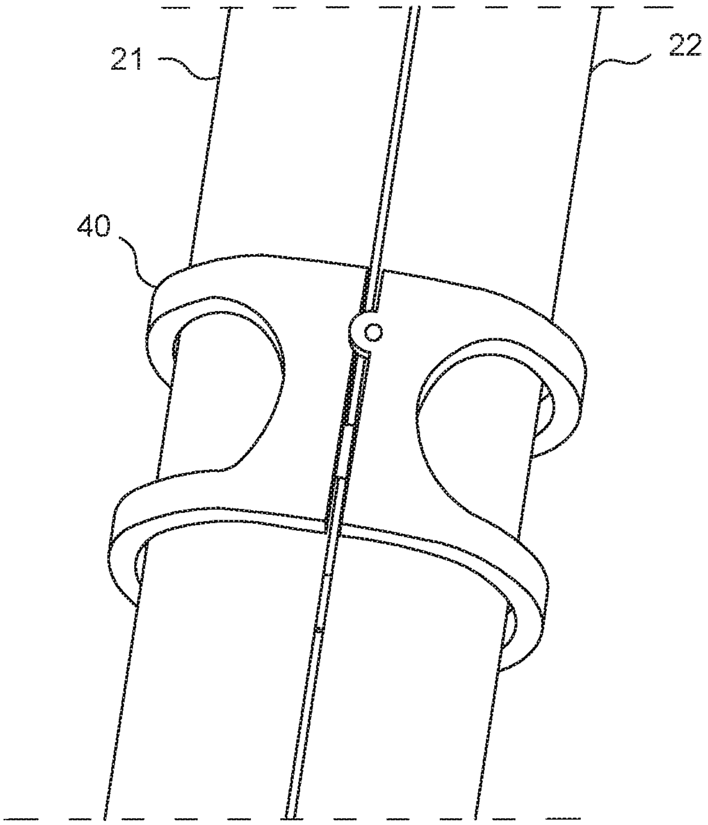
FIG. 11*c* is an oblique view of the clamp of the continuous positive airway pressure (CPAP) cannula device in a latched state when the respiratory tubes are housed within the clamp.
Figure 11D:
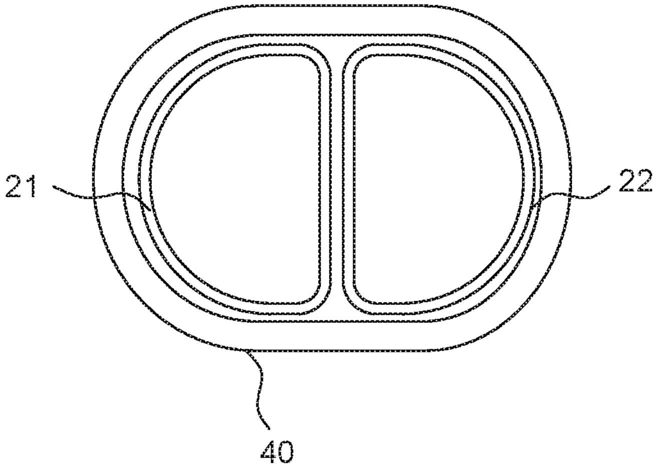
FIG. 11*d* is a plan view of the clamp of the continuous positive airway pressure (CPAP) cannula device in a latched state when the respiratory tubes are housed within the clamp.

Referring now to FIGS. 11*c* and 11*d*, the respiratory tubes 21 and 22 may be housed within the clamp 40 when the clamp 40 is in a latched state.

Although the clamp 40 according to the first preferred embodiment of the CPAP cannula device has been described, any known conventional securing means, such a ring (metal or plastic) for securing the two respiratory tubes 21 and 22 at the converging point corresponding to the respective converging portions 21*b* and 22*b* may be used to secure the two respiratory tubes 21 and 22 together. Alternatively, the CPAP cannula device may be used without a securing means.

Figure 12:
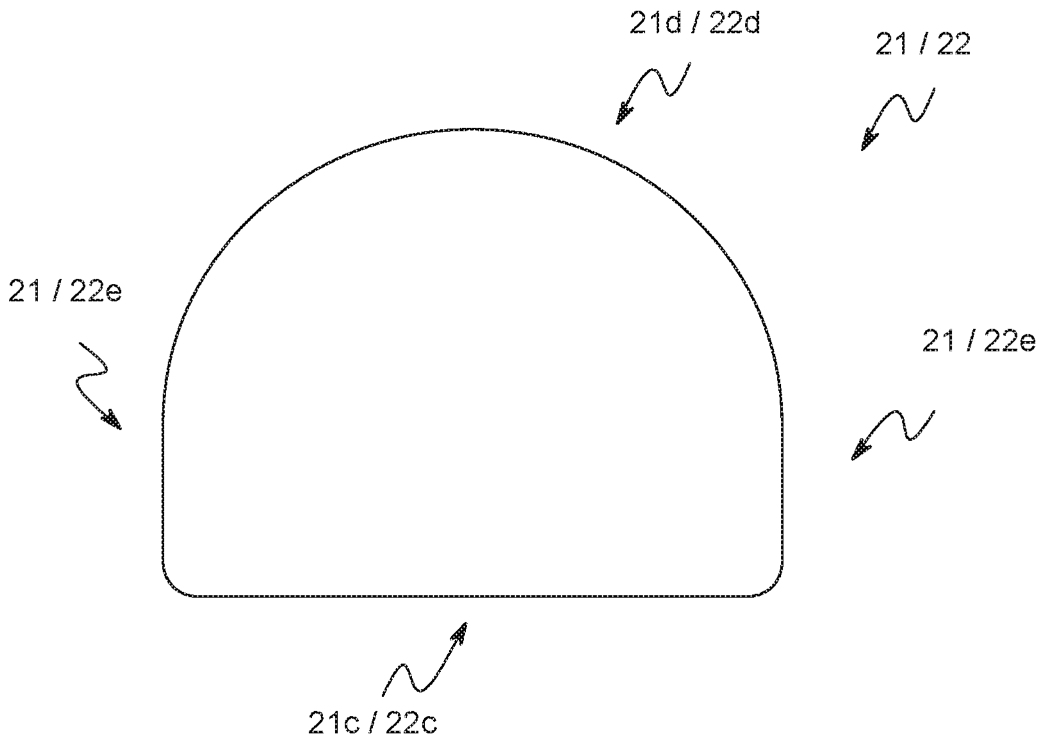
FIG. 12 is a partial cut-away view of one of the respiratory tubes of the continuous positive airway pressure (CPAP) cannula device according to the preferred embodiment taken along the line XII-XII in FIG. 7.
Figure 16:
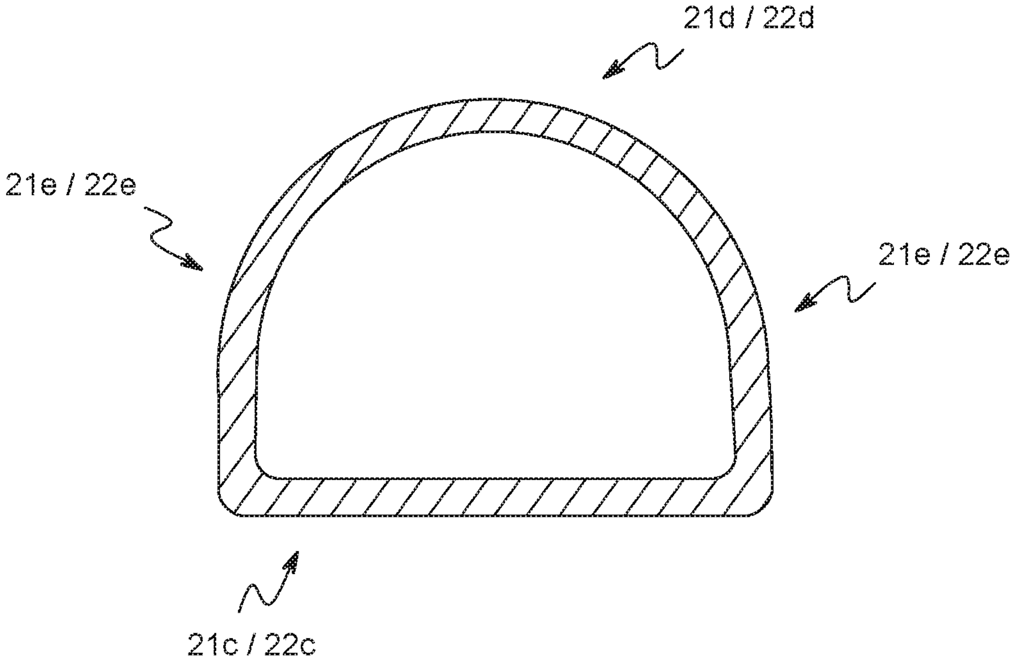
FIG. 16 is a partial cut-away view of one of the respiratory tubes of the continuous positive airway pressure (CPAP) cannula device according to the preferred embodiment taken along the line XII-XII in FIG. 7.

Again referring to the respiratory tubes 21 and 22, as is shown in FIGS. 12 and 16, which are cross-sectional views of one of the respiratory tubes 21 and 22 as viewed in a lengthwise direction from the line XII-XII in FIG. 7, each of the respiratory tubes 21 and 22 comprise a substantially D-shaped cross-section. That is, each of the respiratory tubes 21 and 22 may comprise a bulbous curved portion extending from a flat portion. More specifically, each of the respiratory tubes 21 and 22 comprise a flat portion 21*c* and 22*c*, respectively, a curved portion 21*d* and 22*d*, respectively, and two straight portions 21*e* and 22*e*, respectively. The curved portions 21*d* and 22*d* are half circles with a radius r. At the distal ends of the curved portions 21*d* and 22*d* are straight portions 21*e* and 22*e*. Accordingly, together, the curved portions 21*d*, 22*d*, together with the straight portions 21*e*, 22*e* are not half circles, but rather half circles with a diameter extension configured by the straight portions 21*e*,/22*e*, so as to enhance the cross sectional area and therefore decrease the resistance of gaseous flow. In the preferred embodiment, the curved portions 21*d*, and 22*d* are formed of a radius r, and the straight portion 21*e*, and 22*e* each have a length of one third to one half the radius r. Further, the respiratory tube flat portions 21*c*, and 22*c*, each have a preferred length of about twice the radius r. However, these dimensions may be varies such that the CPAP cannula device fits patients of various sizes An outer flat surface of the flat portion 21*c*/22*c* is configured to rest on the patient's face. This allows the CPAP cannula device to be easily secured via soft friction on the patient and not be displaced or moved easily. Further, as is shown in FIGS. 4 and 10, since the outer flat surface of the flat portion 21*c*/22*c* of the D-shaped cross section design, allows for an increased surface area, as compared to conventional CPAP ventilation systems/devices with tubular design, the CPAP cannula device according to the present embodiment is to be in more contact with the patient's face, this spreads out and reduces the pressing force against the patient's face. This reduces the force supplied by the CPAP cannula device to the patient's face per unit area and reduces injury and irritation to the patient's face.

Figure 8A:
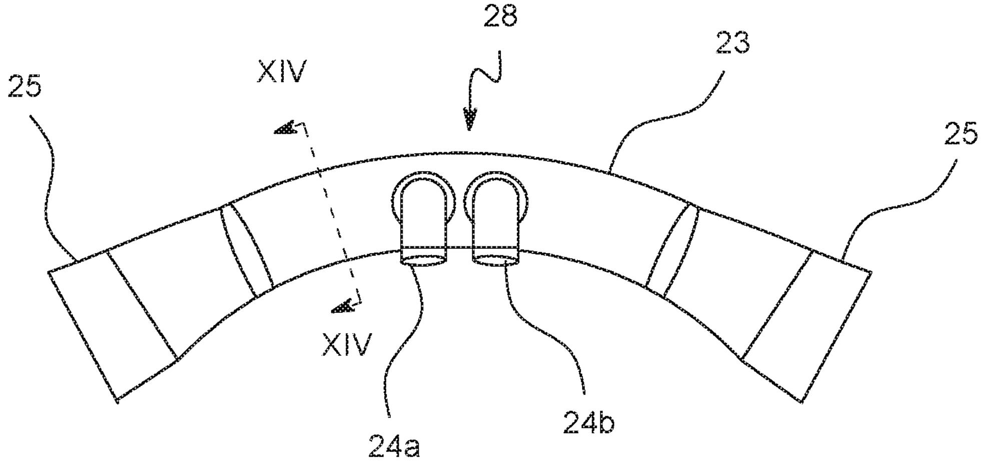
FIG. 8*a* is a front—of the nasal interface of the continuous positive airway pressure (CPAP) cannula device according to the preferred embodiment.
Figure 8B:
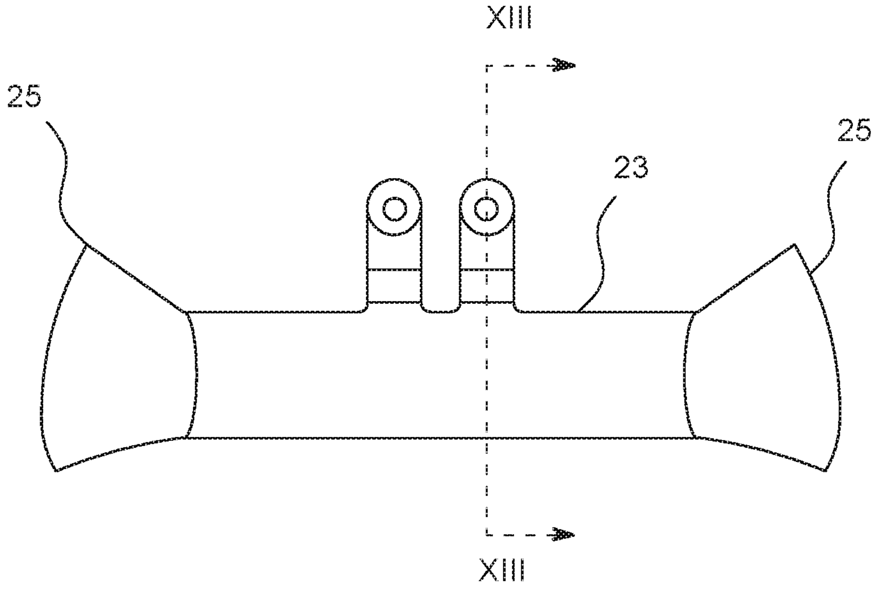
FIG. 8*b* is a below view of the nasal interface of the continuous positive airway pressure (CPAP) cannula device according to the preferred embodiment.

Now again referring to the nasal interface 23, as is shown in FIGS. 8*a* and 8*b*; the nasal interface 23 comprises two extension interfaces 25 which are positioned at the respective ends of the nasal interface 23 in a length-wise direction. Each of the extension interfaces 25 connect to one of the respiratory tubes 21/22 via the respective respiratory tube connecting portions 21*a* and 22*a*. In between each of the extension interfaces 25 is the nasal segment base 26.

Figure 14:
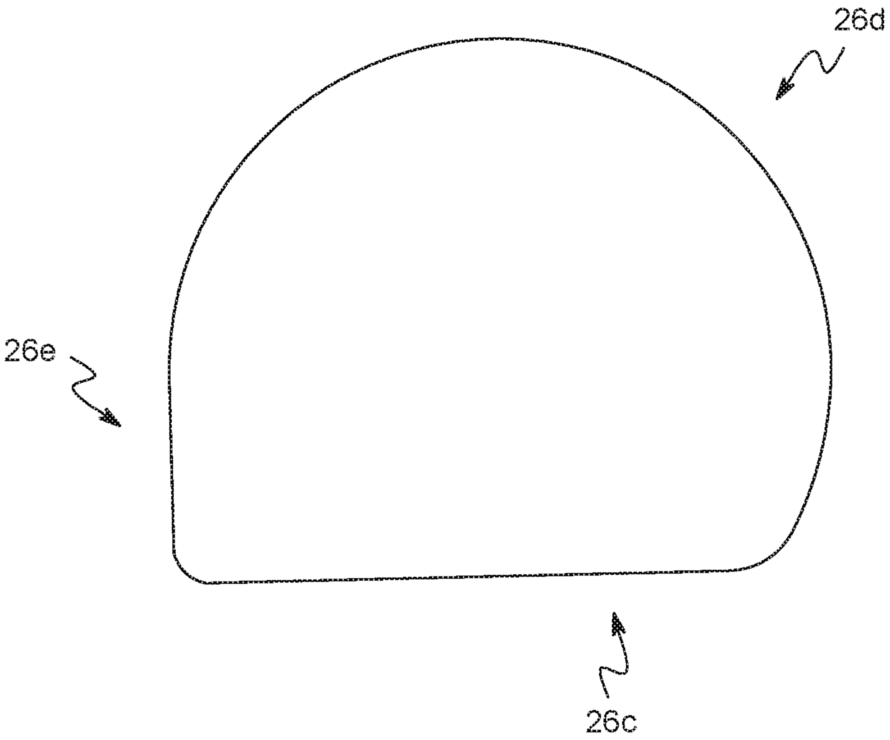
FIG. 14 is a cross-sectional view of the nasal interface of the continuous positive airway pressure (CPAP) cannula device according to the preferred embodiment taken along the line XIV-XIV in FIG. 8*a*.
Figure 19:
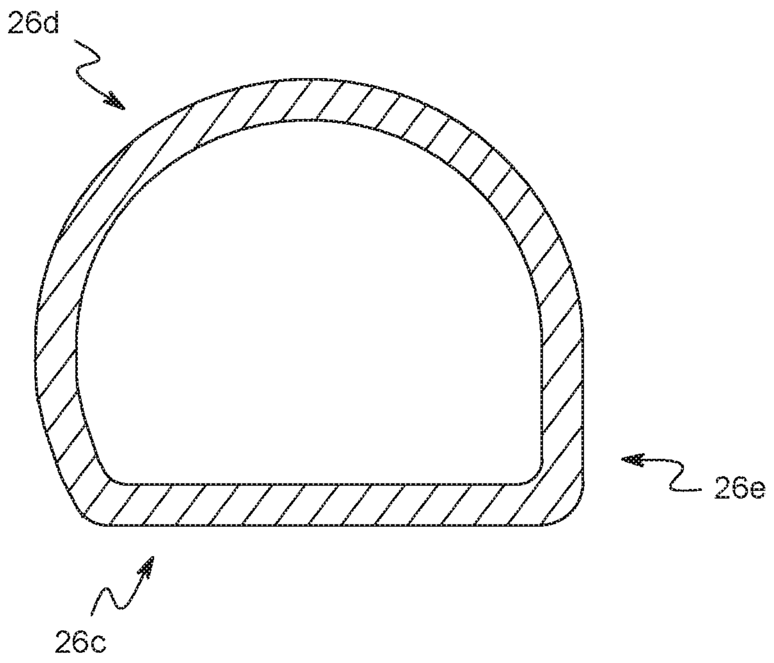
FIG. 19 is a cross-sectional view of the nasal interface of the continuous positive airway pressure (CPAP) cannula device according to the preferred embodiment taken along the line XIV-XIV in FIG. 8*a*.

Referring now to FIG. 14, which is a cross-sectional view of the nasal interface 23 taken along the line XIV-XIV in FIG. 8*a* or FIG. 19, which a mirror view of the same cross-section taken along the line XIV-XIV in FIG. 8*a*, the nasal interface 23, including the extension interfaces 25, is formed into a substantially D-shaped cross section. More specifically, the D-shaped cross-section consists of a curved portion 26*d* having a predetermined outer diameter, a flat base portion 26*c* having a predetermined length, and a straight portion 26*e* having a predetermined length. The D-shaped cross section of the nasal interface 23 is different than the D-shaped cross section of the respiratory tubes 21 and 22. Specifically, the D-shaped cross section of the nasal interface 23 comprises a nasal segment curved portion 26*d* which is formed to have a radius r1. One side of the nasal segment curved portion 26*d* is formed to connect directly to the nasal segment flat base portion. The other side of the nasal segment curved portion 26*d* is formed to connect to the nasal segment base straight portion 26*e*. That is, the nasal segment curved portion 26*d* is formed of an arc extending from the distal end of the nasal segment base straight portion 26*e* to the distal end of the nasal segment flat base portion 26*c*. In the preferred embodiment, the nasal segment flat base portion 26*c* has a slightly longer length than the radius rl of the nasal segment curved portion 26*d*. Also in the preferred embodiment, the nasal segment base straight portion 26*e* has a length slightly shorter than the radius r1 of the nasal segment curved portion 26*d*. However, these dimensions may be varied according to other embodiments of the CPAP cannula device so as to fit the CPAP cannula device to patients of different sizes.

In the preferred embodiment, the nasal segment flat base portion 26*c* is configured to rest against a patient's lip, and the nasal segment base straight portion 26*e* is designed to face the patient's nasal septum without resting or touching it. Further, the nasal prongs 24*a* and 24*b* each extend from the nasal base segment straight portion 26*e*. This design allows for reduced resistance in gaseous flow. Further, since the nasal segment curved portion 26*d* extends on one end to the nasal segment flat base portion 26*c* so as to connect to the nasal segment flat base portion 26*c* in a curved manner, the design allows the CPAP cannula device to better fit on a patient's upper lip so as to not intrude into a patient's mouth opening.

Figure 13:
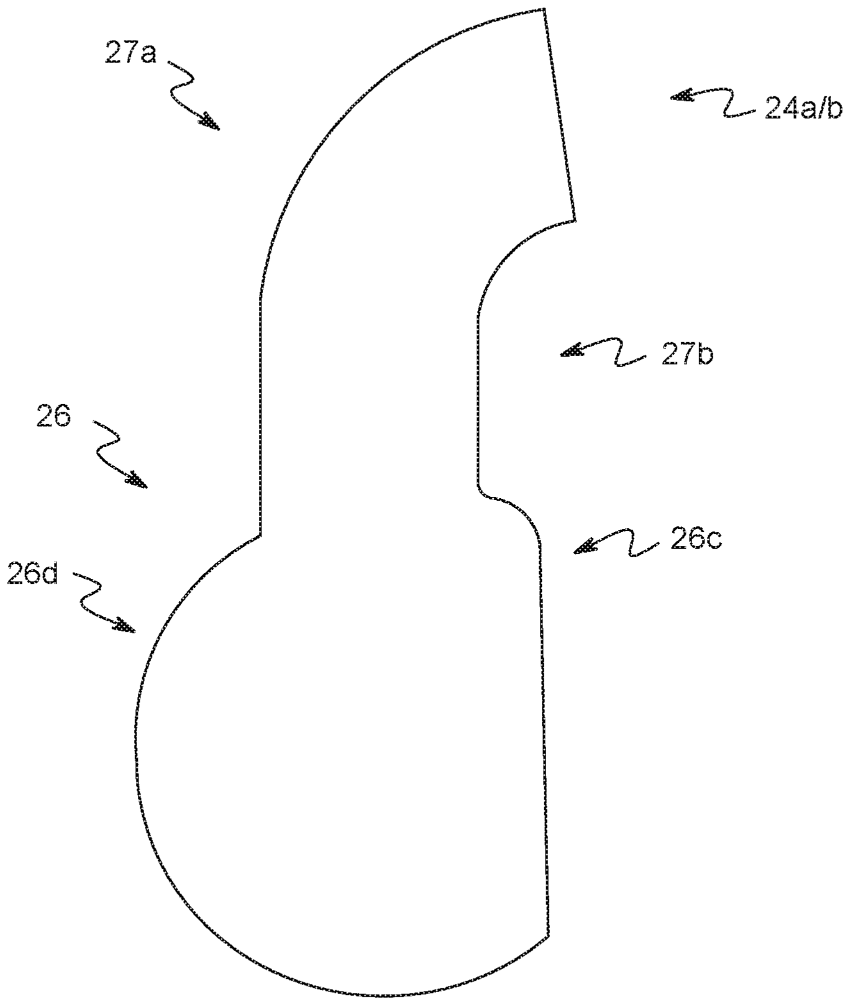
FIG. 13 is a cross-sectional view of one of the nasal prongs of the continuous positive airway pressure (CPAP) cannula device according to the preferred embodiment.

Referring now to FIG. 13, which is a cross-sectional view of the nasal interface 23 taken along the line XIII-XIII in FIG. 8*b*, it will be noticed that the nasal prongs 24*a*, 24*b* extend from a portion where the nasal segment base straight portion 26*e* exists in other portions of the nasal interface 23.

As is shown in FIGS. 4 and 10, the nasal segment flat base portion 26*c* is configured to rest along the patient's upper lip and cheek area. The D-shaped cross sectional design of the nasal interface 23 allows the CPAP cannula device to be easily secured so as to not be displaced or moved from the position on the patient's face and in and out of the patient's nose as its stabilized in place by the combination of snuggly fit prongs in the nose, flat surfaces resting on patient face and head, and the gentle pull toward the rear via the clamp 40 securing both respiratory tubes 21 and 22 together. Further, since the nasal interface 23 has a D-shaped cross section, as described above, and because the nasal segment flat base portion 26*c* of the nasal interface 23 rests against the patient's face, the nasal interface 23 increases the amount of surface area of the CPAP cannula device in contact with the patient's face as compared to conventional CPAP ventilation systems/devices which have cylindrical components which rest against patient's faces. This design reduces the chances of the nasal interface 23 from being displaced back and forth, and therefore reduces the chances that the nasal interface 23 will hit or inflect pressure on the nasal septum causing injury and breakdown. Further, The D-shaped cross section design also spreads out and reduces the pressing force against the patient's face. This reduces the force supplied by the CPAP cannula device to the patient's face per unit area and reduces injury and irritation to the patient's face.

Also, it will be noticed that when referring to FIG. 13, the peculiar D-shaped cross-sectional design of the nasal interface 23 has a shorter base length than the D-shaped cross sectional design of the respiratory tubes 21/22 and therefore allows the nasal interface 23 to preferably rest only against the upper lip of the patient, and not fall below the upper lip of the patient. That is, a curved portion of the nasal interface 23 may extend bulbously and downwardly from the flat portion of the nasal interface tube. This assures better stability and reduces further irritation to the patient.

As mentioned above, the flat portions 21*c* and 22*c* of the respiratory tubes 21 and 22, respectively, as well as the nasal segment flat base portion 26*c* are configured to rest against the patient's face. Such a configuration of the CPAP cannula device allows the CPAP cannula device to be secured on a patient's face via friction with three primary stability points—the upper lip with prongs inside the nose, the outer distal ends of the patient's cheeks, and the rear of the patient's head.

Figure 9:
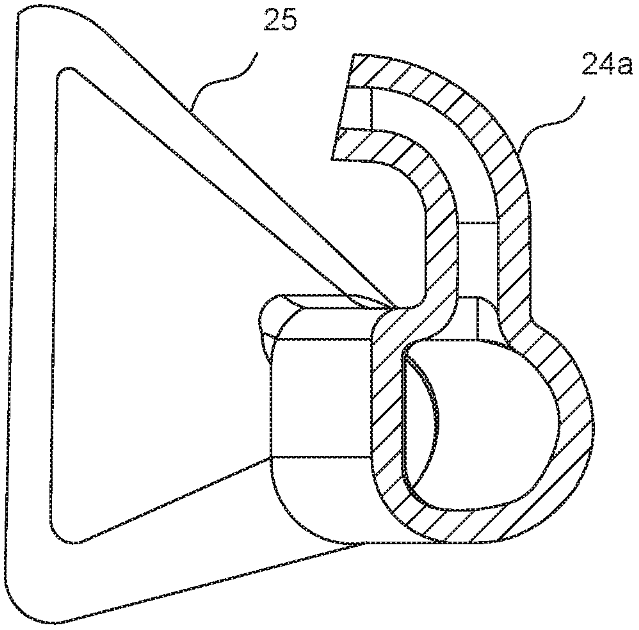
FIG. 9 is a partial cut-away view of the nasal interface of continuous positive airway pressure (CPAP) cannula device according to the preferred embodiment taken along the line XIII-XIII of FIG. 8*b*.

Referring again to the nasal interface 23, it will be noticed with reference to FIGS. 8-9, and 13, that the nasal prongs 24*a* and 24*b* extend radially from the nasal interface 23 initially in a direction parallel to the nasal segment flat base portion 26*c*. More specifically, each of the nasal prongs 24*a* and 24*b* extend radially initially in a direction parallel to the nasal segment flat base portion 26*c* before curving at a predetermined length toward a direction substantially perpendicular to the nasal segment flat base portion 26*c* at a predetermined radius R. That is, the nasal prongs 24*a* and 24*b* each have a nasal prong's upperside length 27*a* extending radially from the nasal segment curved portion 26*d* to the distal end of the nasal prongs 24*a* and 24*b*. The nasal prongs 24*a* and 24*b* each also have a nasal prong's underside length 27*b* extending radially from the nasal segment flat base portion 26*c*. Such a configuration of the nasal prongs 24*a* and 24*b* allow the nasal prongs to be inserted by a predetermined distance into the patient's nares. The nasal prongs 24*a* and 24*b* are sized such that the nasal prongs 24*a* and 24*b* extend into the patient's nares in a direction parallel to the patient's nares by a predetermined distance. Such a configuration further allows the CPAP cannula device to be easily secured to a patient while reducing irritation to the patient.

That is, since the nasal prongs 24*a* and 24*b* extend radially from the nasal interface 23 that rests with a flat surface on the upper lip and stabilized by the respiratory tubes 21, 22 on both sides on the cheeks and the back of the head, the nasal interface 23 is restricted from rocking backward and forward against the patient's septum. This prevents damage to the patient's nasal septum and allows the CPAP cannula device to be secured to the patient.

Further, the nasal prongs 24*a* and 24*b* are each sized to have a predetermined outer diameter and a predetermined inner diameter such that the nasal prongs 24*a* and 24*b* fit snugly (i.e. cover approximately 100% of the patient's nares) in the patient's nares.

The sizing of the aforementioned components of the CPAP cannula device can be varied such that the system fits patients of different sizes. Below is a table representing the appropriate sizing of different component for use in newborn patients of corresponding various sizes. It will be noted that the below table is presented as showing possible or suggested sizes of the CPAP cannula device according to the preferred embodiment. However, it will also be noted that the dimensions/diameters of the component of the CPAP cannula device may be while staying within the spirit of the CPAP cannula device.

TABLE 1

| Size | Patient Weight | NSFBP | NSBCP | POD | PT | NPID | NPUL | RTL | RTFP | RTCP |
|---|---|---|---|---|---|---|---|---|---|---|
| 0 | <600 | 6.5 | 7.5 | 3.2 | 0.6 | 2.4 | 12.0 | 15.0 | 15.0 | 5.0 |
| 1 | 600-750 | 7.0 | 7.5 | 3.6 | 0.7 | 2.7 | 14.0 | 15.0 | 15.0 | 5.0 |
| 2 | 750-1000 | 7.5 | 8.0 | 4.0 | 0.8 | 3.3 | 16.0 | 15.0 | 15.0 | 5.0 |
| 3 | 1000-1500 | 8.0 | 9.0 | 4.5 | 0.9 | 4.5 | 18.0 | 15.0 | 15.0 | 5.0 |
| 4 | 1500-2500 | 9.0 | 10.0 | 5.0 | 1.0 | 5.0 | 20.0 | 15.0 | 15.0 | 5.0 |
| 5 | >2500 | 10.0 | 12.0 | 5.5 | 1.0 | 5.5 | 24.0 | 15.0 | 15.0 | 5.0 |

In the Table 1 above, the size corresponds to an arbitrary sizing number for reference during manufacturing, sale, or use of the CPAP cannula device. The patient weight refers to a patient's, here a neonate's, weight in grams. The NSFBP refers to the length of the nasal segment flat base portion 26*c* in millimeters (mm). The NSBCP refers to the diameter in mm of the nasal segment curved portion 26*d* from a portion of the bottom of the nasal segment curved portion 26*d*, as shown, for example, in FIG. 13, to a portion where the nasal prong upperside length 27*a* begins. The POD refers to the outer diameter in mm of the nasal prongs 24*a*, 24*b*. The PT refers to the thickness of the nasal prongs 24*a*, 24*d* in mm. The NPID refers to the length of the nasal prongs intra distance 28 in mm. The NPUL refers to the length of the nasal prongs upperside length 27*a* in mm. The RTL refers to the length of each of the respiratory tubes 21, 22 in mm. The RTFP refers to the length of the respiratory tube flat portion 21*c*, 22*c* in mm. The RTCP refers to the diameter of the respiratory tube curved portions 21*d*, 22*d*, in mm. While the above table presents six different sizes of the CPAP cannula device according to the preferred embodiment, the CPAP cannula device according to the preferred embodiment is not so limited. Rather, the above-table merely presents example sizes of the CPAP cannula device to be used for newborn infants.

According to another preferred embodiment of the CPAP cannula device, the D-shaped cross section of the nasal interface 23 is the same shape as the D-shaped cross section of the respiratory tubes 21 and 22.

According to another preferred embodiment of the CPAP cannula device, the nasal interface section 23 may be indented in the nasal prongs intra distance portion 28 to further protect the patient's nasal septum. That is, the nasal segment base straight portion may be indented.

According to another preferred embodiment of the CPAP cannula device, the distal ends of the nasal prongs 24*a* and 24*b* may be terminated at the end configured to be inserted into the patient's nares in a predetermined angle such that the distal ends of the nasal prongs 24*a* and 24*b* are not in parallel to the nasal segment flat base portion 26*c*. Though the distal ends of the nasal prongs 24*a* and 24*b* may also be in parallel to the nasal segment flat base portion 26*c*.

While the material comprising the CPAP cannula device is preferably silicon, other similar materials may be used, such as poly-vinyl-chloride (PVC) or any other material that is suitable for ease of manufacturing and patient safety.

According to another preferred embodiment of the CPAP cannula device, the nasal prongs 24*a* and 24*b* may be formed to be stiffer and more resilient than the other portions of the CPAP cannula device.

Figure 15A:
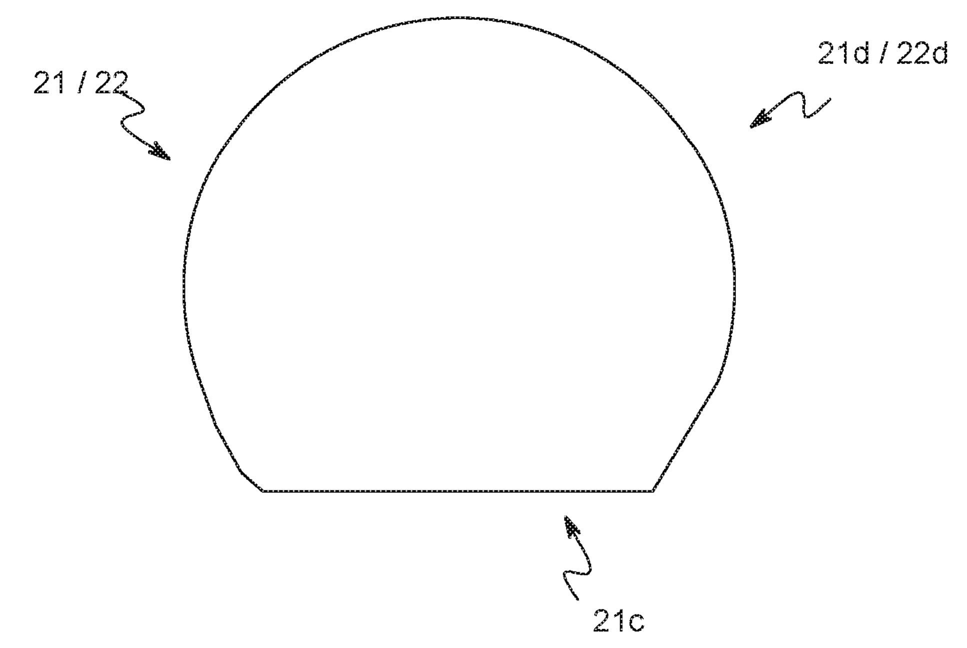
FIG. 15*a* is a partial cut-away view of one of the respiratory tubes of the continuous positive airway pressure (CPAP) cannula device according to an alternative embodiment taken along the line XII-XII in FIG. 7.
Figure 18:
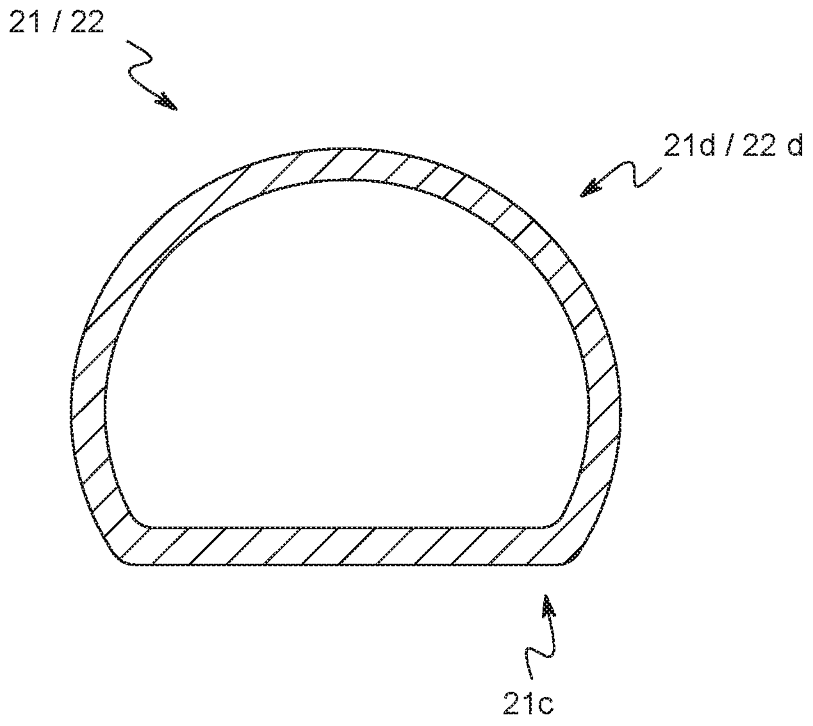
FIG. 18 is a partial cut-away view of one of the respiratory tubes of the continuous positive airway pressure (CPAP) cannula device according to an alternative embodiment taken along the line XII-XII in FIG. 7.

According to an alternative embodiment of the CPAP cannula device, the respiratory tubes 21 and 22 may have a different cross-sectional design. This design may still comprise bulbous curved portion extending from a flat portion. Specifically, according to this alternative embodiment, referring now to FIGS. 15*a* and 18, which are cross-sectional views of one of the respiratory tubes 21 and 22 as viewed in a length-wise direction from the line XII-XII in FIG. 7, each of the respiratory tubes comprises a substantially C-shaped cross-section. More specifically, in this alternative embodiment, the respiratory tube curved potion 21*d*/22*d* extends from the distal ends of the respiratory tube flat portion 21*c*/22*c*. That is, the respiratory tube curved portion 21*d*/22*d* is formed by an arc with a predetermined radius R extending from the distal ends of the respiratory tube flat portion 21*c*/22*c*. Such a design allows for a shorter respiratory tube flat portion 21*c*/22*c*, accordingly this allows for a smaller CPAP cannula device. All other features of the CPAP cannula device as described above apply to this alternative embodiment.

Figure 15B:
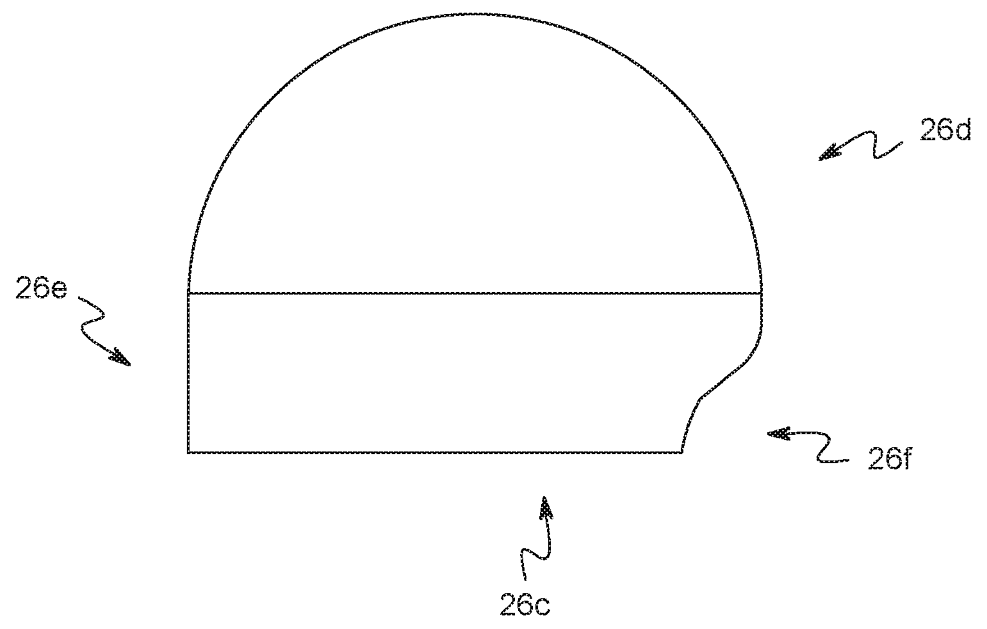
FIG. 15*b* is a cross-sectional view of the nasal interface of the continuous positive airway pressure (CPAP) cannula device according to an alternative embodiment taken along the line XIV-XIV in FIG. 8*a*.

According to another alternative embodiment, of the CPAP cannula device the nasal interface 23 may have a different cross-sectional design. Specifically, according to this alternative embodiment, now referring to FIG. 15*b*, which is a cross-sectional view of the nasal interface 23 taken along the line XIV-XIV in FIG. 8*a*, the nasal interface 23, including the extension interfaces 25, is formed into a substantially modified D-shaped cross section. More specifically, in this alternative embodiment, the nasal interface curved portion 26*d* connects on the end not connected to the nasal segment base straight portion 26*e*, via a nasal segment concave curve portion 26*f*. The nasal segment concave curve portion 26*f* is formed in a shape of a concave curve. The nasal segment concave curve portion 26*f* may also be replaced with a straight line diagonal portion which connects the nasal interface curved portion 26*d* on the end not connected to the nasal segment base straight portion 26*e*, to the nasal interface flat base portion. Such a design allows for a shorter nasal segment flat base portion 26*c*, accordingly this allows for a smaller CPAP cannula device for smaller patients. All other features of the CPAP cannula device as described above apply to this alternative embodiment.

Figure 17:
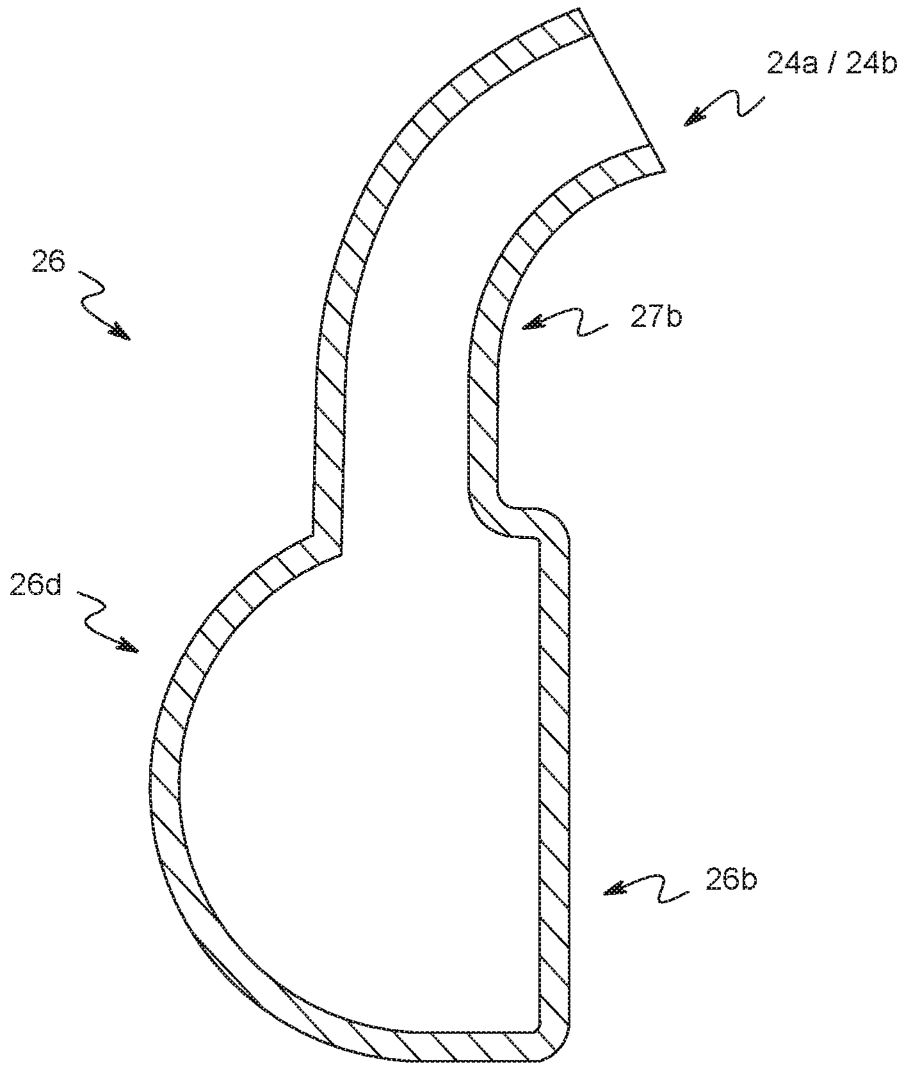
FIG. 17 is a cross-sectional view of one of the nasal prongs of the continuous positive airway pressure (CPAP) cannula device according to an alternative embodiment.

According to another alternative embodiment, of the CPAP cannula device, the nasal interface 23 may have a different cross-sectional design. Specifically, the cross-section design of the nasal interface, as shown in FIG. 13, may be modified as shown in FIG. 17, which is a cross-sectional view of one of the nasal prongs of the continuous positive airway pressure (CPAP) cannula device according to the instant alternative embodiment. Specifically, the nasal segment curved portion 26*d* may connect on one end to the nasal segment flat base portion 26*c* via a short straight segment.

As described above, and with instant reference to FIG. 3, the continuous positive airway pressure (CPAP) cannula device 1 may also further comprise a first transitioning segment 301 and a second transitioning segment 302, wherein the first transitioning segment 301 connects the nasal interface 23 on one end to the first respiratory tube 21, and the second transitioning segment 302 connects the nasal interface on another end thereof to the second respiratory tube 22.

Those in the art will understand that a number of variations may be made in the disclosed embodiments, all without departing from the scope and spirit of the invention, which is defined solely by the appended claims. Further, while the above-described embodiments are directed toward a CPAP cannula device that alleviates the need to secure said system to a patient's face without the use of a securing means, as opposed to conventional CPAP ventilation systems/devices which often utilized a hat, pins, tapes, or other special connectors to fix the system in a stable position, it will be understood by those skilled in the relevant art that the instantly described embodiments of the CPAP cannula device may also include a means to fasten the device to a patient. Such fastening could be achieved with tape, Tagaderm®, or any other conventional fastening means. Further still, while the described embodiments of the CPAP cannula device have been primary described as for use with neonates and infants, those skilled in the relevant art will readily understand that the device can be modified without departing from the spirit of the disclosure such that the device can be used on a wide spectrum of patients including adults.

REFERENCE NUMERALS

1: continuous positive airway pressure (CPAP) device;
21: respiratory tube;
21*a:* respiratory tube connecting portion;
21*b* respiratory tube converging portion;
21*c:* respiratory tube flat portion;
21*d:* respiratory tube curved portion;
21*e:* respiratory tube straight portion;
22: respiratory tube;
22*a:* respiratory tube connecting portion;
22*b* respiratory tube converging portion;
22*c:* respiratory tube flat portion;
22*d:* respiratory tube curved portion;
22*e:* respiratory tube straight portion;
23: nasal interface;
24*a:* nasal prong;
24*b:* nasal prong;
25: extension interface;
26: nasal segment base;
26*c:* nasal segment flat base portion;
26*d:* nasal segment curved portion;

26*e:* nasal segment base straight portion;
26*f:* nasal segment concave curve portion
27*a:* nasal prong upperside length;
27*b:* nasal prong underside length
28: nasal prongs intra distance;
40: clamp;
41: claim swinging portion;
42: clamp swinging portion;
43: clamp hinge;
47: clamp mating device;
47*a:* clamp mating device pin;
47*b:* clamp mating device pin hole;
100: conventional CPAP system/device;
93: nasal interface of conventional CPAP system/device;
94*a:* nasal prong of conventional CPAP system/device;
94*b:* nasal prong of conventional CPAP system/device;
112: respiratory tube of conventional CPAP system/device;
112*a:* connecting elbow of conventional CPAP system/device;
114: respiratory tube of conventional CPAP system/device;
114*a:* connecting elbow of conventional CPAP system/device;
144: securing means of conventional CPAP system/device
124: second securing means of a conventional CPAP system/device (hat)
146: chin securing strap of conventional CPAP system/device.

What is claimed is:

1. A continuous positive airway pressure (CPAP) cannula device comprising:

a first respiratory tube for inspiration and a second respiratory tube for expiration;

a nasal interface tube provided between the first and second respiratory tubes; and two nasal prongs extending radially from the nasal interface tube;

wherein the respiratory tubes, the nasal interface tube, and the nasal prongs are integrated with each other so as to comprise a one-piece design, the one-piece design being formed in a U shape configured to curve around a patient's face in a backward and upward direction, with distal ends of the two respiratory tubes converging toward each other, and the respiratory tubes each having an inflection point where the direction of extension changes, wherein each of the respiratory tubes and the nasal interface tube have a D-shaped cross section, wherein each of the respiratory tubes have an equal or larger diameter than a diameter of a center portion of the nasal interface tube, wherein the nasal interface tube includes a flat portion configured to rest against a patient's upper lip and cheek area and a curved portion, the flat portion and the curved portion forming the D-shaped cross section of the nasal interface tube, the curved portion extending downward from the flat portion, below a bottom end of the flat portion, and extending outward in a direction perpendicular to a plane in which the flat portion is disposed, and wherein the nasal prongs include a straight portion and a curved portion, the straight portion of the nasal prongs extending from the flat portion which is configured to rest against the patient's upper lip and cheek area and in a same direction in which the flat portion of the nasal interface tube extends.

2. The continuous positive airway pressure (CPAP) cannula device according to claim 1, wherein from respective portions connecting to the nasal interface tube, each of the first and second respiratory tubes is formed to extend in a direction perpendicular to a direction in which the nasal interface tube extends, and perpendicular to a direction in which the nasal prongs extend from the nasal interface tube, before extending to a position corresponding to the patient's cheeks to a position corresponding to a back upper part of the patient's head, when the CPAP cannula device is worn by the patient.

3. The continuous positive airway pressure (CPAP) cannula device according to claim 1, wherein flat portions of each of the respiratory tubes, having the D-shaped cross section, are configured to rest against the patient's face.

4. The continuous positive airway pressure (CPAP) cannula device according to claim 1, wherein each of the two nasal prongs comprises a nasal upperside length and a nasal underside length, and wherein the nasal upperside length is longer than the nasal underside length.

5. The continuous positive airway pressure (CPAP) cannula device according to claim 1, further comprising a clip;

wherein flat portions of the respective two respiratory tubes, having the D-shaped cross-section, are configured to rest against each other and are secured to each other by the clip.

6. The continuous positive airway pressure (CPAP) cannula device according to claim 1, wherein the nasal interface is indented in between the nasal prongs.

7. The continuous positive airway pressure (CPAP) cannula device according to claim 1, further comprising a first transitioning segment and a second transitioning segment, wherein the first transitioning segment connects the nasal interface tube on one end to the first respiratory tube, and the second transitioning segment connects the nasal interface tube on another end to the second respiratory tube, and wherein each of the first and second transitioning segments have a larger diameter at one respective end thereof as compared to another respective end thereof.

8. The continuous positive airway pressure (CPAP) cannula device according to claim 7, wherein the nasal interface tube has either a same or different cross-sectional shape than each of the first and second respiratory tubes.

9. The continuous positive airway pressure (CPAP) cannula device according to claim 1, wherein flat portions of the first and second respiratory tubes and the flat portion of the nasal interface tube form an aligned continuous flat surface configured to rest against the patient's face.

10. The continuous positive airway pressure (CPAP) cannula device according to claim 1, wherein the curved portion of the nasal interface tube extends bulbously and downwardly from the flat portion of the nasal interface tube.

11. The continuous positive airway pressure (CPAP) cannula device according to claim 1, wherein each of the nasal prongs has an outer diameter in the range of 3.2 to 5.5 mm, inclusive.

12. The continuous positive airway pressure (CPAP) cannula device according to claim 1, wherein the nasal interface tube has a diameter in the range of 7.5 to 12 mm, inclusive.

13. The continuous positive airway pressure (CPAP) cannula device according to claim 3, wherein respective portions of each of the two nasal prongs, which are connected to the nasal interface tube extend in a direction parallel to the nasal segment flat base portion of the nasal interface tube.

14. The continuous positive airway pressure (CPAP) cannula device according to claim 1, wherein at least the D-shaped cross section of the respiratory tubes has two parallel straight sections joined by a curved section.

15. The continuous positive airway pressure (CPAP) cannula device according to claim 1, wherein at least the D-shaped cross section of the respiratory tubes has a straight section joined by a curved section.

16. The continuous positive airway pressure (CPAP) cannula device according to claim 1, wherein the D-shaped cross section of the respiratory tubes includes a half circle shape on top of a rectangular shape.

17. The continuous positive airway pressure (CPAP) cannula device according to claim 1, wherein the CPAP cannula device is configured to be secured to the patient's head via frictional contact with the patient's head at three stability points.

18. The continuous positive airway pressure (CPAP) cannula device according to claim 17, the three stability points including contact points between the CPAP cannula device and the patient's head at the patient's upper lip, outer distal ends of the patient's cheeks, and the rear of the patient's head.

19. The continuous positive airway pressure (CPAP) cannula device according to claim 1, wherein the CPAP cannula device is configured to be secured to the patient's head without the use of a securing means.

20. The continuous positive airway pressure (CPAP) cannula device according to claim 17, wherein the CPAP cannula device is configured to be secured to the patient's head without the use of a securing means.

21. The continuous positive airway pressure (CPAP) cannula device according to claim 18, wherein the CPAP cannula device is configured to be secured to the patient's head without the use of a securing means.

* * * * *